United States Patent [19]
Yamaguchi et al.

[11] Patent Number: 5,963,334
[45] Date of Patent: Oct. 5, 1999

[54] APPARATUS AND METHOD FOR MEASURING COLOR OF A MEASUREMENT OBJECT

[75] Inventors: Wataru Yamaguchi, Toyokawa; Mitsunobu Ota, Shinshiro, both of Japan

[73] Assignee: Minolta Co., Ltd., Osaka, Japan

[21] Appl. No.: 09/034,393

[22] Filed: Mar. 4, 1998

[30] Foreign Application Priority Data

Mar. 7, 1997 [JP] Japan ..................................... 9-053360

[51] Int. Cl.[6] ..................................................... G01N 21/25
[52] U.S. Cl. ......................... 356/425; 356/402; 356/405; 356/407; 250/306
[58] Field of Search ..................................... 356/425, 402, 356/405, 406, 407, 445–448; 250/306, 210, 560; 358/101, 93

[56] References Cited

U.S. PATENT DOCUMENTS 4,583,858   4/1986   Lebling et al. .

FOREIGN PATENT DOCUMENTS 63-41019   8/1988   Japan .
5-80614   11/1993   Japan .

Primary Examiner—Frank G. Font
Assistant Examiner—Layla Lauchman
Attorney, Agent, or Firm—Burns, Doane, Swecker & Mathis, LLP

[57] ABSTRACT

A color measuring apparatus is provided with a radial illumination unit for projecting illumination light to a measurement object at a first illumination angle in a plurality of directions, a unidirectional illumination unit for projecting illumination light to the measurement object at a second illumination angle in a single direction, a unidirectional light receiving unit for receiving a light ray reflected at a first angle $\theta 1$ from the direction of regular reflection out of illumination light projected from the radial illumination unit and reflected by the measurement object, and a light ray reflected at a second angle $\theta 2$ from the direction of regular reflection out of illumination light projected from the unidirectional illumination unit and reflected by the measurement object, the second angle $\theta 2$ being larger than the first angle $\theta 1$, and a processing unit for calculating a color value at the first angle $\theta 1$ and a color value at the second angle $\theta 2$ based on an output of the unidirectional light receiving unit.

23 Claims, 9 Drawing Sheets

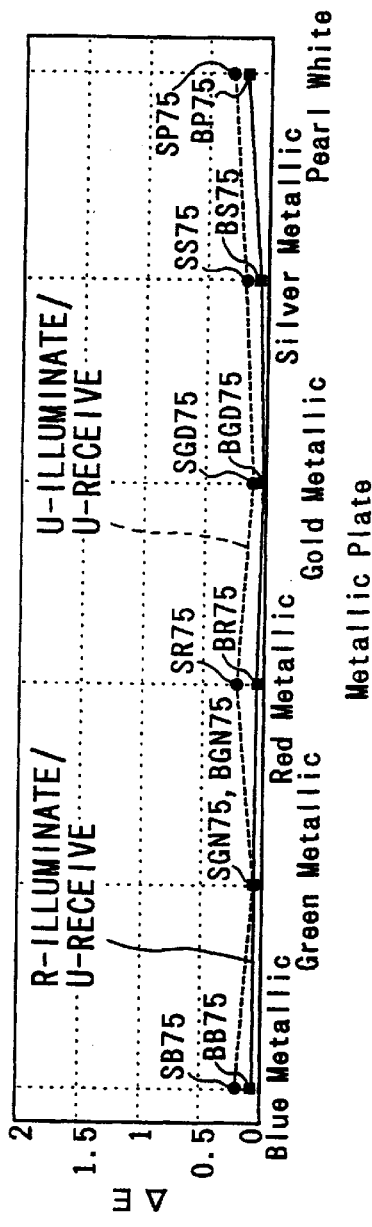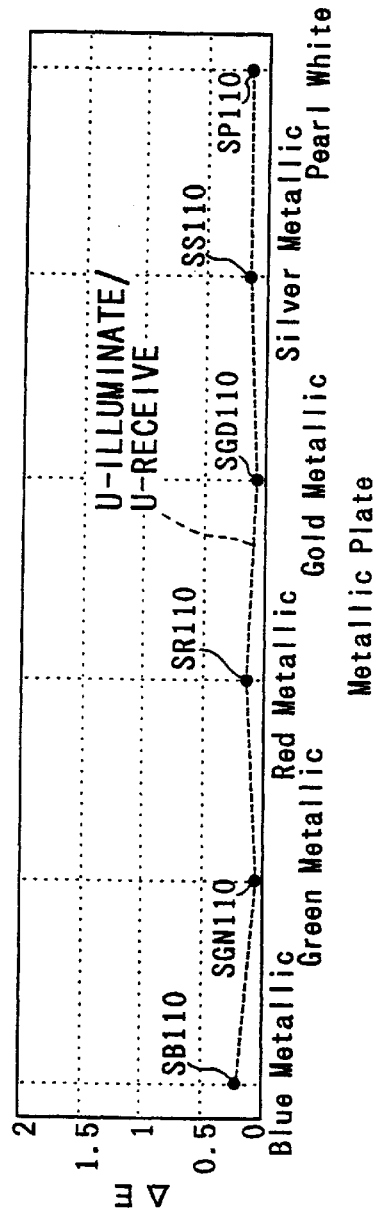

1

1

1

1

APPARATUS AND METHOD FOR MEASURING COLOR OF A MEASUREMENT OBJECT

This application is based on patent application No. 9-53360 filed in Japan, the contents of which is hereby incorporated by reference.

BACKGROUND OF THE INVENTION

This invention relates to a color measuring apparatus and method for measuring color of a measurement object having an angular metamerism, such as metallic coating, in which aluminum flakes or mica flakes in a coating.

There have been known color measuring apparatuses for a metallic coating. A color measuring apparatus disclosed in Japanese Examined Patent Publication No. 63(SHO)-41019 measures color of a coating as follows: Illumination light is projected from a single illumination light source onto a coating as a measurement object. Among the light rays reflected by the coating, reflected light rays which are reflecting in a plurality of angular directions different from a direction of regular reflection are received by a plurality of light receiving elements. Color of the coating is measured based on signals outputted from the respective light receiving elements. This color measuring apparatus is of the unidirectional illumination/radial light reception type.

A color measuring apparatus disclosed in Japanese Examined Patent Publication No. 4(HEI)-29019 measures color of a coating as follows: Illumination light rays are intermittently projected at angles different from each other to a coating as a measurement object. Light rays reflected by the coating are successively received by a single light receiving element, and color of the coating is measured based on signals successively outputted from the light receiving element. This color measuring apparatus is of the radial illumination/unidirectional light reception type.

Further, a color measuring apparatus disclosed in Japanese Examined Patent Publication No. 5(HEI)-80614 measures color of a coating as follows: An illumination light ray is projected to a measurement object in one direction. A reflected light ray which is inclined by a specified angle from a direction of regular reflection is received by a light receiving element. Color of the coating is measured based on an output signal of this light receiving element. This color measuring apparatus is of the unidirectional illumination/unidirectional light reception type.

In the color measuring apparatus of the unidirectional illumination/unidirectional light reception type, if the metallic coating is illuminated in one direction, there arises a major problem of considerable angle dependency of the reflected light in the case that light is not reflected in a uniform direction in a range near the direction of regular reflection due to the orientation of bright material such as aluminum flakes or mica flakes, in the case that the surface of the measurement object is curved, in the case that the color measuring apparatus is slightly inclined, or other case.

The color measuring apparatus of the unidirectional illumination/radial light reception type is free from the above problem because light rays reflected in different directions are measured although the measurement object is illuminated in one direction, and color of the measurement object is measured based on the output signals of the light receiving elements having received the respective reflected light rays. The same can be said of the color measuring apparatus of the radial illumination/unidirectional light reception type.

In the conventional color measuring apparatuses of the unidirectional illumination/radial light reception type, light receiving elements are also arranged in a range near the direction of regular reflection (e.g., directions at 25° or 45° from the direction of regular reflection) and in a range relatively distant from the direction of regular reflection (e.g., 75° from the direction of regular reflection), so as to enable the radial light reception. This makes the construction of the apparatus complicated, resulting in a larger size and an increased production cost.

Further, in the color measurement, it is essential to receive reflected light rays at angles larger than 90° from the direction of regular reflection of the illumination light by the light receiving element and to measure color based on the output signals of the light receiving elements to evaluate the color performance in the thickness of a coating. This measurement is hereinafter called "color-in-thickness measurement." However, the conventional color measuring apparatuses are incapable of performing the color-in-thickness measurement due to its construction.

SUMMARY OF THE INVENTION

It is an object of the present invention to provide a color measuring apparatus which has overcome the problems residing in the prior art.

It is another object of the present invention to provide a color measuring apparatus which can measure color of a measurement object in a simplified construction and can accompany a reduced production cost.

It is another object of the present invention to provide a color measuring apparatus which can perform the color-in-thickness measurement as well as usual measurements.

According to an aspect of the present invention, an apparatus for measuring color of a measurement object, the apparatus comprises: a first radial illumination unit which projects illumination light to a measurement object at a first illumination angle in a plurality of directions different from one another; a unidirectional illumination unit which projects illumination light to the measurement object at a second illumination angle in a single direction, the second illumination angle being different from the first illumination angle; a first unidirectional light receiving unit which receives a light ray reflected at a first angle θ1 from the direction of regular reflection out of illumination light projected from the first radial illumination unit and reflected by the measurement object, and a light ray reflected at a second angle θ2 from the direction of regular reflection out of illumination light projected from the unidirectional illumination unit and reflected by the measurement object, the second angle θ2 being larger than the first angle θ1; and a processing unit which executes: calculation of a color value at the first angle θ1 based on an output of the first unidirectional light receiving unit by permitting the first radial illumination unit to project illumination light to the measurement object; and calculation of a color value at the second angle θ2 based on an output of the first unidirectional light receiving unit by permitting the unidirectional illumination unit to project illumination light to the measurement object.

According to another aspect of the present invention, a method for measuring color of a measurement object, comprises the steps: projecting illumination light to a measurement object at a first illumination angle in a plurality of directions different from one another; receiving a light ray reflected at a first angle θ1 from the direction of regular reflection out of illumination light reflected by the measurement object, outputting an electrical signal corresponding to the received light ray; calculating a color value at the first angle θ1 based on the outputted electrical signal; projecting illumination light to the measurement object at a second illumination angle in a single direction, the second illumination angle being different from the first illumination angle; receiving a light ray reflected at a second angle θ2 from the direction of regular reflection out of illumination light reflected by the measurement object, the second angle θ2 being larger than the first angle θ1; outputting an electrical signal corresponding to the received light ray; and calculating a color value at the second angle θ2 based on the outputted electrical signal.

These and other objects, features and advantages of the present invention will become more apparent upon a reading of the following detailed description and accompanying drawings.

BRIEF DESCRIPTION OF THE DRAWINGS

FIGS. 2A and 2B are respectively graphs showing comparisons of measurement results at 75° and 110° in the case that color differences (ΔE) are measured by the color measuring apparatus of the radial illumination/unidirectional light reception type and in the case that color differences (ΔE) are measured by the color measuring apparatus of the unidirectional illumination/unidirectional light reception type;

DETAILED DESCRIPTION OF THE PREFERRED EMBODIMENTS OF THE INVENTION

Before describing embodiments of the invention, the basic principle of the invention will be first described.

A. Basic Principle of the Invention

FIGS. 1 and 2 are graphs showing comparisons of measurement results in the case that color differences (ΔE) are measured by a color measuring apparatus of the radial illumination/unidirectional light reception type and in the case that color differences (ΔE) are measured by a color measuring apparatus of the unidirectional illumination/unidirectional light reception type. The shown results were obtained by the measurements under the following conditions. Six kinds of metallic coatings (blue metallic coating, green metallic coating, red metallic coating, gold metallic coating, silver metallic coating, pearl white metallic coating) were prepared. The color value of each coating was measured in the radial illumination/unidirectional light reception by a CM-512m3 manufactured by MINOLTA Co., Ltd. while the coating was rotated every 90°. The color value of each coating was also measured in the unidirectional illumination/unidirectional light reception by a CM-512m1 or CM-512m2 manufactured by MINOLTA Co., Ltd. while the coating was rotated every 90°. Color differences ΔE were obtained by calculating deviations from a reference value.

Figure 3A:
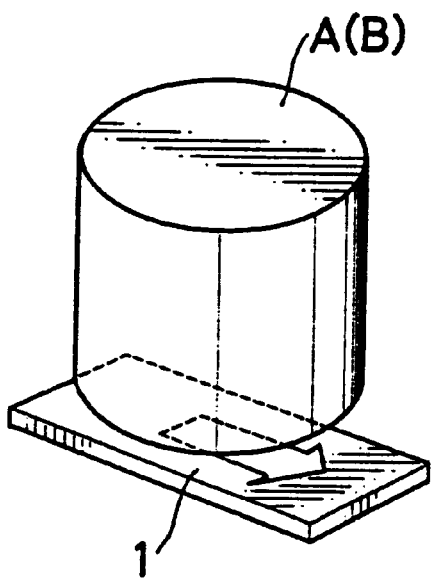
FIGS. 3A to 3D are diagrams showing measurement conditions of FIGS. 1A and 2B.
Figure 3C:
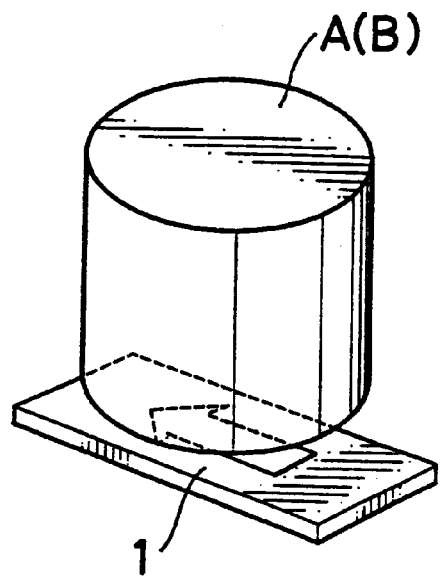
Figure 3B:
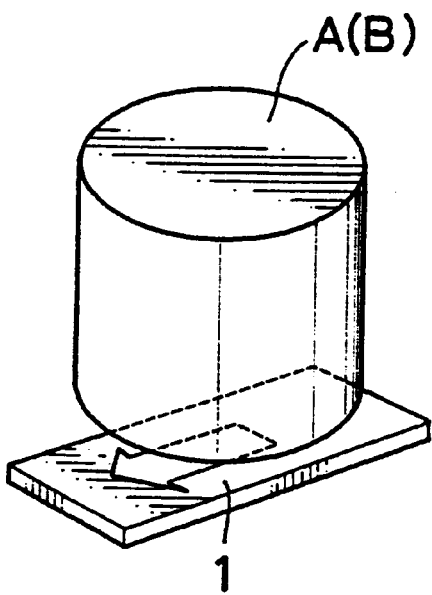
Figure 3D:
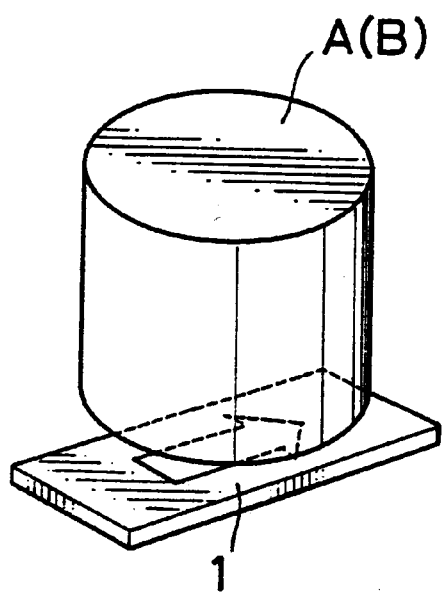

A-1. Measurement of Color Differences in Radial Illumination/Unidirectional Light Reception Specifically, a blue metallic coating (i.e., measurement object) is first placed in position P0 as shown in FIG. 3A. The color value is measured by the measuring apparatus A (CM-512m3). Light rays reflected at 25°, 45° and 75° from a direction of regular reflection are successively received by the light receiving elements, and the color values are obtained.

α(Blue, P0, 25°),

α(Blue, P0, 45°), and

α(Blue, P0, 75°).

In FIG. 3A, an arrow is a virtual sign drawn to visually clarify the orientation of a coating 1. The state shown in FIG. 3A is position P0; the state obtained by rotating the coating 1 clockwise by 90° from the position P0 is position P90, the state obtained by rotating the coating 1 clockwise from the position P0 by 180° is position P180; and the state obtained by rotating the coating 1 clockwise from the position P0 by 270° is position P270.

Next, after the same coating 1 is set in the position P90, the coating 1 is measured by the measuring apparatus A (CM-512m3), and the light rays reflected at 25°, 45° and 75° from the direction of regular reflection are successively received by the light receiving elements, and the color values are obtained.

α(Blue, P90, 25°),

α(Blue, P90, 45°), and

α(Blue, P90, 75°).

Further, while the same coating 1 is successively set in the positions P180, P270, the light rays reflected at 25°, 45° and 75° from the direction of regular reflection are similarly successively received by the light receiving elements, and the color values are obtained.

α(Blue, P180, 25°),

α(Blue, P180, 45°),

α(Blue, P180, 75°),

α(Blue, P270, 25°),

α(Blue, P270, 45°), and

α(Blue, P270, 75°).

Figure 1A:
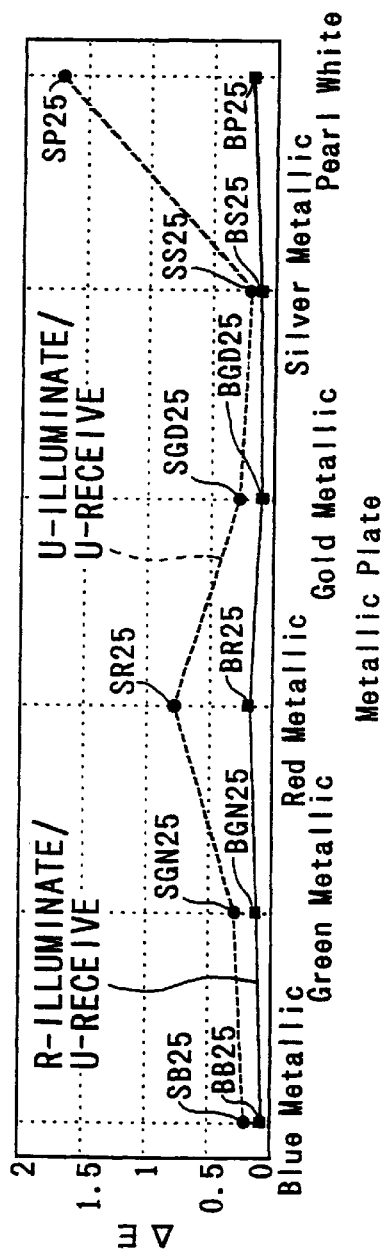
FIGS. 1A and 1B are respectively graphs showing comparisons of measurement results at 25° and 45° in the case that color differences (ΔE) are measured by a color measuring apparatus of the radial illumination/unidirectional light reception type and in the case that color differences (ΔE) are measured by a color measuring apparatus of the unidirectional illumination/unidirectional light reception type.

Using α(Blue, P0, 25°) as a reference, deviations from this reference value, i.e., color differences ΔE(Blue, P90, 25°), ΔE(Blue, P180, 25°) and ΔE(Blue, P270, 25°) are calculated:

$\Delta E(\text{Blue}, \text{P90}, 25°) = |\alpha(\text{Blue}, \text{P90}, 25°) - \alpha(\text{Blue}, \text{P0}, 25°)|,$ $\Delta E(\text{Blue}, \text{P180}, 25°) = |\alpha(\text{Blue}, \text{P180}, 25°) - \alpha(\text{Blue}, \text{P0}, 25°)|,$ and $\Delta E(\text{Blue}, \text{P270}, 25°) = |\alpha(\text{Blue}, \text{P270}, 25°) - \alpha(\text{Blue}, \text{P0}, 25°)|.$ Then, ΔE(Blue, 25°) is calculated by averaging these color differences. The thus obtained ΔE is a measurement result obtained when the blue metallic coating 1 is measured by the radial illumination/unidirectional light reception (at an angle of 25° from the direction of regular reflection). In FIG. 1A, a square point BB25 corresponds to this measurement result.

Figure 1B:
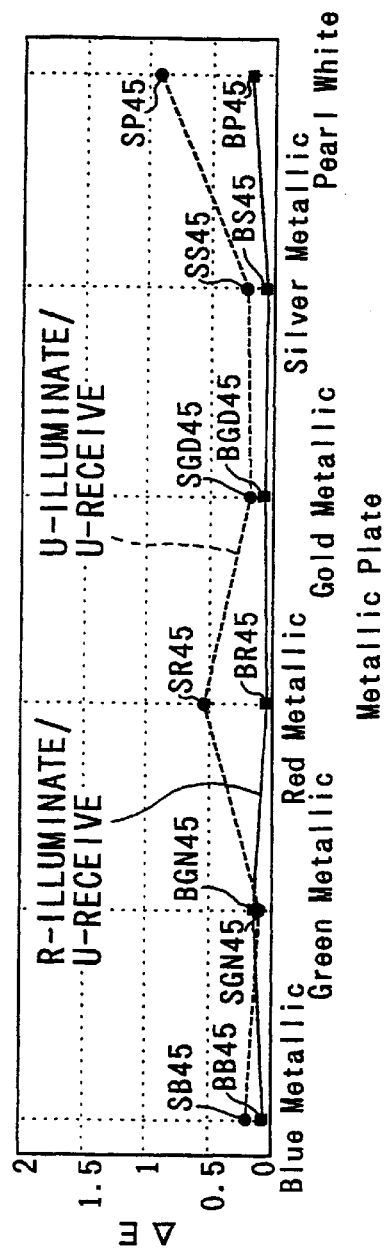

In a manner similar to the above, using α(Blue, P0, 45°) as a reference, deviations from this reference value, i.e., color differences ΔE(Blue, P90, 45°), ΔE(Blue, P180, 45°) and ΔE(Blue, P270, 45°) are calculated. Then, ΔE(Blue, 45°) is calculated by averaging these color differences. In FIG. 1B, a square point BB45 corresponds to ΔE(Blue, 45°)

In a manner similar to the above, using α(Blue, P0, 75°) as a reference, deviations from this reference value, i.e., color differences ΔE(Blue, P90, 75°), ΔE(Blue, P180, 75°) and ΔE(Blue, P270, 75°) are calculated. Then, ΔE(Blue, 75°) is calculated by averaging these color differences. In FIG. 2A, a square point BB75 corresponds to ΔE(Blue, 75°).

The measurement results of the blue metallic coating by the radial illumination/unidirectional light reception are described above. Measurement results are obtained for other coatings in the similar manner and are plotted in FIGS. 1A, 1B, and 2A. Specifically, in FIGS. 1A to 2A, the measurements results of the color differences of the green metallic coating at the respective angles of 25°, 45°°and 75° correspond to square points BGN25, BGN45 and BGN75. The measurements results of the color differences of the red metallic coating at the respective angles of 25°, 45° and 75° correspond to square points BR25, BR45 and BR75. The measurements results of the color differences of the gold metallic coating at the respective angles of 25°, 45° and 75° correspond to square points BGD25, BGD45 and BGD75. The measurements results of the color differences of the silver metallic coating at the respective angles of 25°, 45° and 75° correspond to square points BS25, BS45 and BS75. The measurements results of the color differences of the pearl white metallic coating at the respective angles of 25°, 45° and 75° correspond to square points BP25, BP45 and BP75.

A-2. Measurements of Color Differences in the Unidirectional Illumination/Unidirectional Light Reception Here, similar to the above case "Measurement in the Radial Illumination/Unidirectional Light Reception", the blue metallic coating 1 is first placed in position P0 as shown in FIG. 3A and is measured by the measuring apparatuses B(CM-512m1 or CM-512m2). Color values are obtained by successively receiving light rays reflected in directions, which are at 25°, 45°, 75° and 110° from the direction of regular reflection, by the light receiving elements:

β(Blue, P0, 25°),

β(Blue, P0, 45°),

β(Blue, P0, 75°), and

β(Blue, P0, 110°).

Further, while the same coating is successively set in positions P90, P180, P270, color values are obtained by successively receiving light rays reflected in directions, which are at 25°, 45°, 75° and 110° from the direction of regular reflection, by the light receiving elements in manners similar to the above:

β(Blue, P90, 25°),

β(Blue, P90, 45°),

β(Blue, P90, 75°),

β(Blue, P90, 110°),

β(Blue, P180, 25°),

β(Blue, P180, 45°),

β(Blue, P180, 75°),

β(Blue, P180, 110°),

β(Blue, P270, 25°),

β(Blue, P270, 45°),

β(Blue, P270, 75°), and

β(Blue, P270, 110°).

Using β(Blue, P0, 25°) as a reference, deviations amounts from this reference value, i.e., color differences ΔE(Blue, P90, 25°), ΔE(Blue, P180, 25°) and ΔE(Blue, P270, 25°) are calculated:

$\Delta E(\text{Blue}, \text{P90}, 25°) = |\beta(\text{Blue}, \text{P90}, 25°) - \beta(\text{Blue}, \text{P0}, 25°)|,$ $\Delta E(\text{Blue}, \text{P180}, 25°) = |\beta(\text{Blue}, \text{P180}, 25°) - \beta(\text{Blue}, \text{P0}, 25°)|,$ and $\Delta E(\text{Blue}, \text{P270}, 25°) = |\beta(\text{Blue}, \text{P270}, 25°) - \beta(\text{Blue}, \text{P0}, 25°)|.$ Then, ΔE(Blue, 25°) is calculated by averaging these color differences. The thus obtained ΔE is a measurement result obtained when the blue metallic coating 1 is measured by the unidirectional illumination/unidirectional light reception (at an angle of 25° from the direction of regular reflection). In FIG. 1A, a round point SB25 corresponds to this measurement result.

In a manner similar to the above, using β(Blue, P0, 45°) as a reference, deviations from this reference value, i.e., color differences ΔE(Blue, P90, 45°), ΔE(Blue, P180, 45°) and ΔE(Blue, P270, 45°) are calculated. Then, ΔE(Blue, 45°) is calculated by averaging these color differences. In FIG. 1B, a round point SB45 corresponds to ΔE(Blue, 45°).

In a manner similar to the above, using β(Blue, P0, 75°) as a reference, deviations from this reference value, i.e., color differences ΔE(Blue, P90, 75°), ΔE(Blue, P180, 75°) and ΔE(Blue, P270, 75°) are calculated. Then, ΔE(Blue, 75°) is calculated by averaging these color differences. In FIG. 2A, a round point SB75 corresponds to ΔE(Blue, 75°).

In a manner similar to the above, using β(Blue, P0, 110°) as a reference, deviations from this reference value, i.e., color differences ΔE(Blue, P90, 110°), ΔE(Blue, P180, 110°) and ΔE(Blue, P270, 110°) are calculated. Then, ΔE(Blue, 110°) is calculated by averaging these color differences. In FIG. 2B, a round point SB110 corresponds to ΔE(Blue, 110°).

The measurement results of the blue metallic coating by the unidirectional illumination/unidirectional light reception are described above. Measurement results are obtained for other coatings in the similar manner and are plotted in FIGS. 1A to 2B. Specifically, in FIGS. 1A to 2B, the measurements results of the color differences of the green metallic coating at the respective angles of 25°, 45°, 75° and 110° correspond to round points SGN25, SGN45, SGN75 and SGN110. The measurements results of the color differences of the red metallic coating at the respective angles of 25°, 45°, 75° and 110° correspond to round points SR25, SR45, SR75 and SR110. The measurements results of the color differences of the gold metallic coating at the respective angles of 25°, 45°, 75° and 110° correspond to round points SGD25, SGD45, SGD75 and SGD110. The measurement results of the color differences of the silver metallic coating at the respective angles of 25°, 45°, 75° and 110° correspond to round points SS25, SS45, SS75 and SS110. The measurements results of the color differences of the pearl white metallic coating at the respective angles of 25°, 45°, 75° and 110° correspond to round points SP25, SP45, SP75 and SP110.

A-3. Study Based on the Measurement Results (FIGS. 1A to 2B)

As is clear from the measurement results shown in FIGS. 1A to 2B, the color differences ΔE in the measurements by the radial illumination/unidirectional light reception (solid line in FIGS. 1A to 2A) are smaller than those in the measurements by the unidirectional illumination/ unidirectional light reception (dotted line in FIGS. 1A to 2B) as a whole. Particularly, this tendency is seen eminent in the case of, e.g., 25° or 45° which is a relatively smaller angle with respect to the direction of regular reflection. This means that the color of a measurement object can be measured by the radial illumination/unidirectional light reception with fewer errors and better accuracy in the case that the color measurements are performed using light rays reflected near the direction of regular reflection.

Contrary to this, in the case of, e.g., 75° which is a relatively larger angle from the direction of regular reflection, the color differences ΔE are small both in the measurements by the radial illumination/unidirectional light reception (solid line in FIGS. 1A to 2A) and in the measurements by the unidirectional illumination/unidirectional light reception (dotted line in FIGS. 1A to 2B) despite the difference between these measurements. This means that color of a measurement object can be measured with high accuracy regardless of which colorimetry method is used.

Accordingly, it can be said that, in the case that a color measurement is performed using reflection light rays relatively distant from the direction of regular reflection, color of a measurement object can be measured with substantially the same high accuracy by both the radial illumination and the unidirectional illumination.

Although the measurements by the radial illumination/ unidirectional light reception and those by the unidirectional illumination/unidirectional light reception are described by means of comparisons in the above description, the same can be said of the measurements by the unidirectional illumination/radial light reception. In other words, color of the measurement object can be measured with substantially the same high accuracy by both the radial illumination and the unidirectional illumination.

B. First Embodiment

Figure 4:
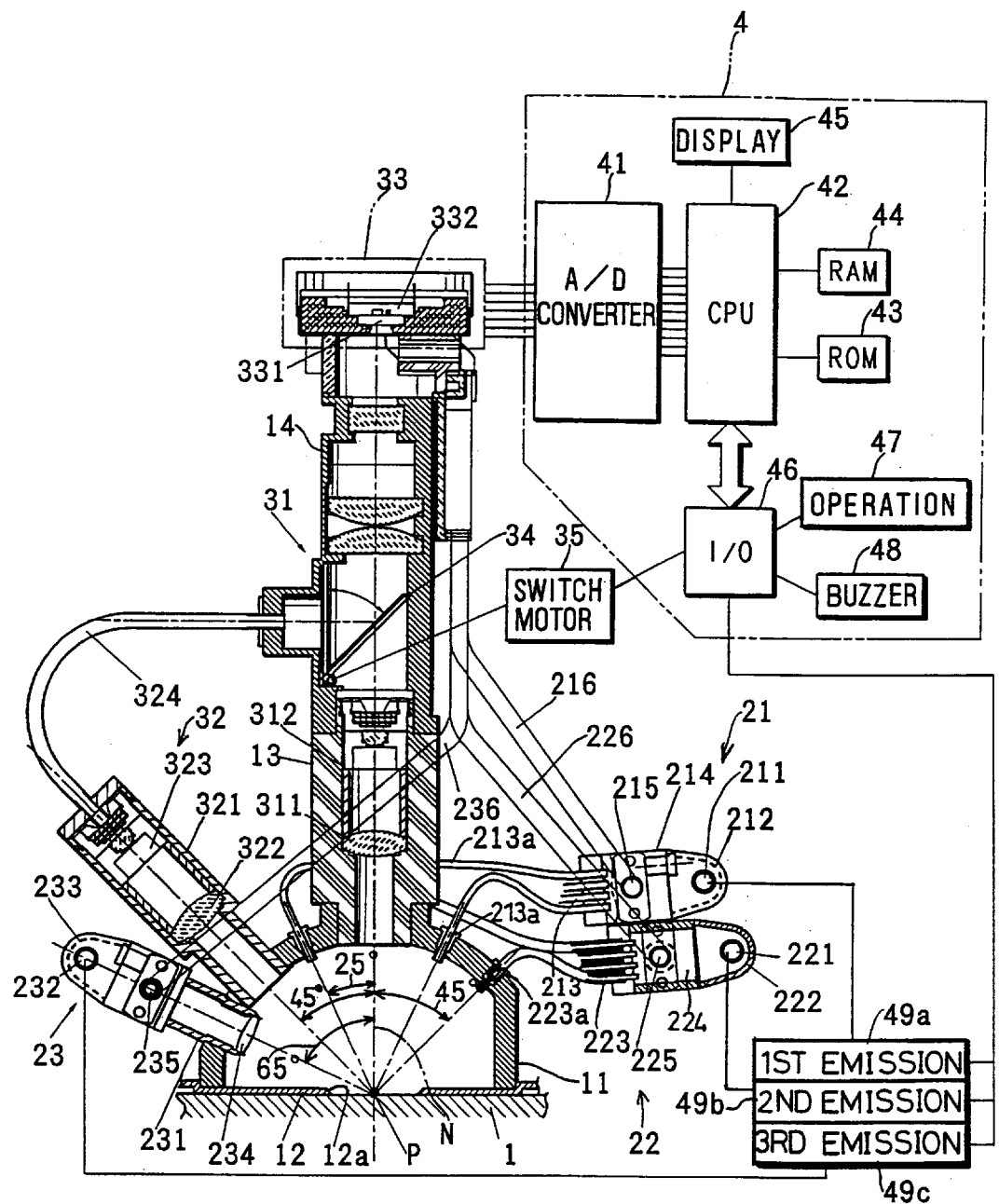
FIG. 4 is a diagram showing a color measuring apparatus according to an embodiment of the invention.

FIG. 4 is a diagram showing a construction of a color measuring apparatus according to a first embodiment of the invention.

This color measuring apparatus is provided with an optical base which is so finished as to have a cup-like shape. A measurement stabilizing leg 12 mounted at the opening side (bottom side of FIG. 4) of the optical base 11 is brought into contact with the surface of a measurement object 1. Illumination light is incident on a measurement area P of the measurement object 1 through an aperture 12a provided substantially in the center of the measurement stabilizing leg 12, and light reflected by the measurement object 1 is returned to the optical base 11. The leg 12 is covered by a soft member made of, e.g., a resin material, so that it can be brought into contact with the surface of the measurement object 1 without scratching. At the bottom side (upper side in FIG. 4) of the optical base 11, first and second barrels 13, 14 for receiving light are continuously placed along vertical direction and constructed such that the light reflected by the measurement object 1 and returned to the optical base 11 is introduced to light receiving elements to be described later.

In this color measuring apparatus, two radial illumination units 21, 22 and one unidirectional illumination unit 23 are provided as an illumination optical system for projecting illumination light to the measurement object 1 as described above.

The radial illumination unit 21 is provided with a first xenon lamp 211 which functions as a light source. A reflector 212 is mounted on this xenon lamp 211 to ensure an amount of light emitted from the xenon lamp 211 and make it uniform. Opposite to the xenon lamp 211 and the reflector 212 is arranged one end of a fiber bundle 213 made by bundling a plurality of optical fibers. The illumination light emitted from the xenon lamp 211 is directly incident on this fiber bundle 213, and the illumination light emitted from the xenon lamp 211 and reflected by the reflector 212 is also incident thereon. In this embodiment, a barrel 214 for monitoring is fixed between the xenon lamp 211 and the fiber bundle 213. A part of the illumination light is extracted through a hole 215 formed in the side surface of the barrel 214 and introduced to the light receiving elements by a fiber 216 for monitoring.

Figure 5:
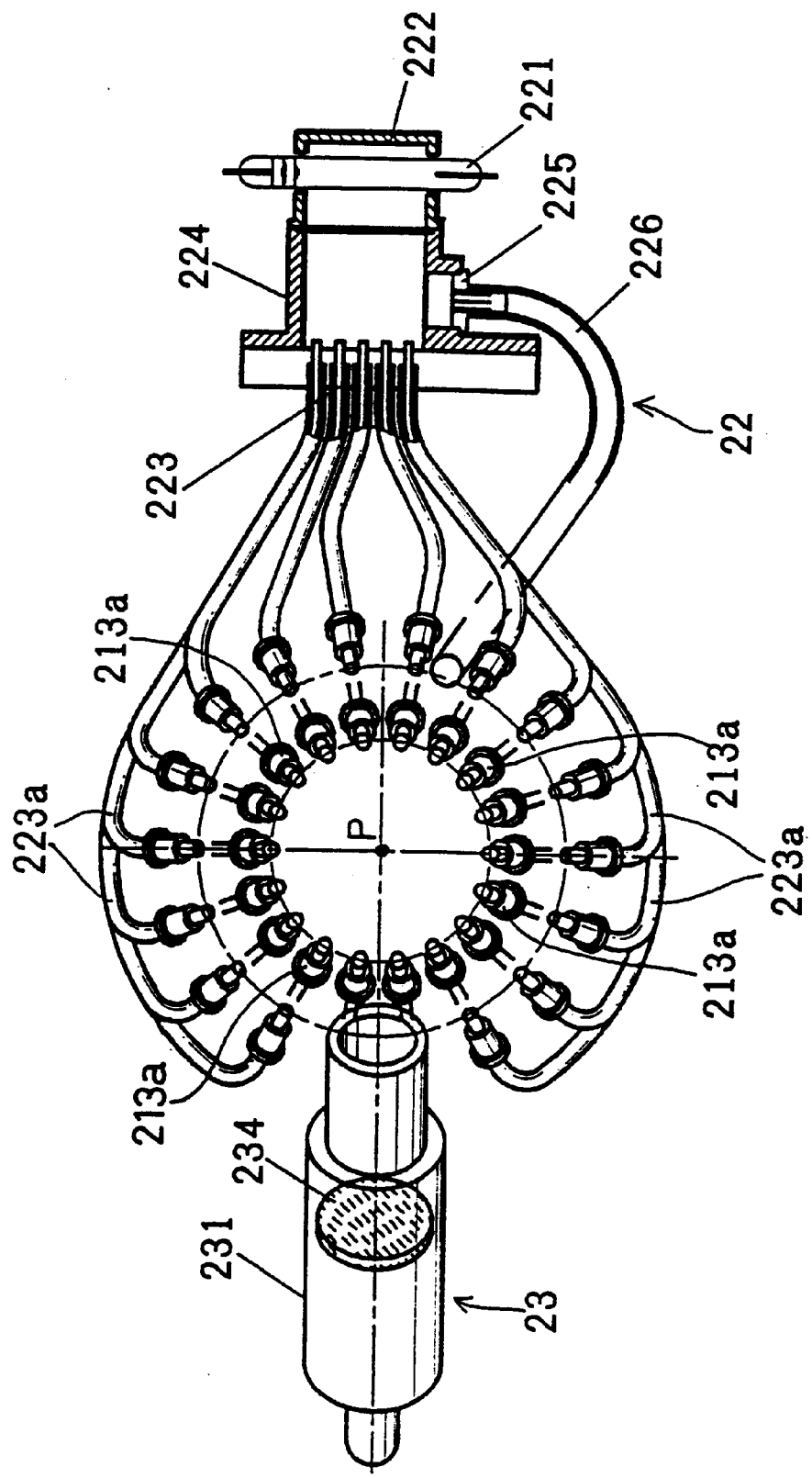
FIG. 5 is a diagram showing an arrangement of three illumination units constructing an illumination optical system.
Figure 6:
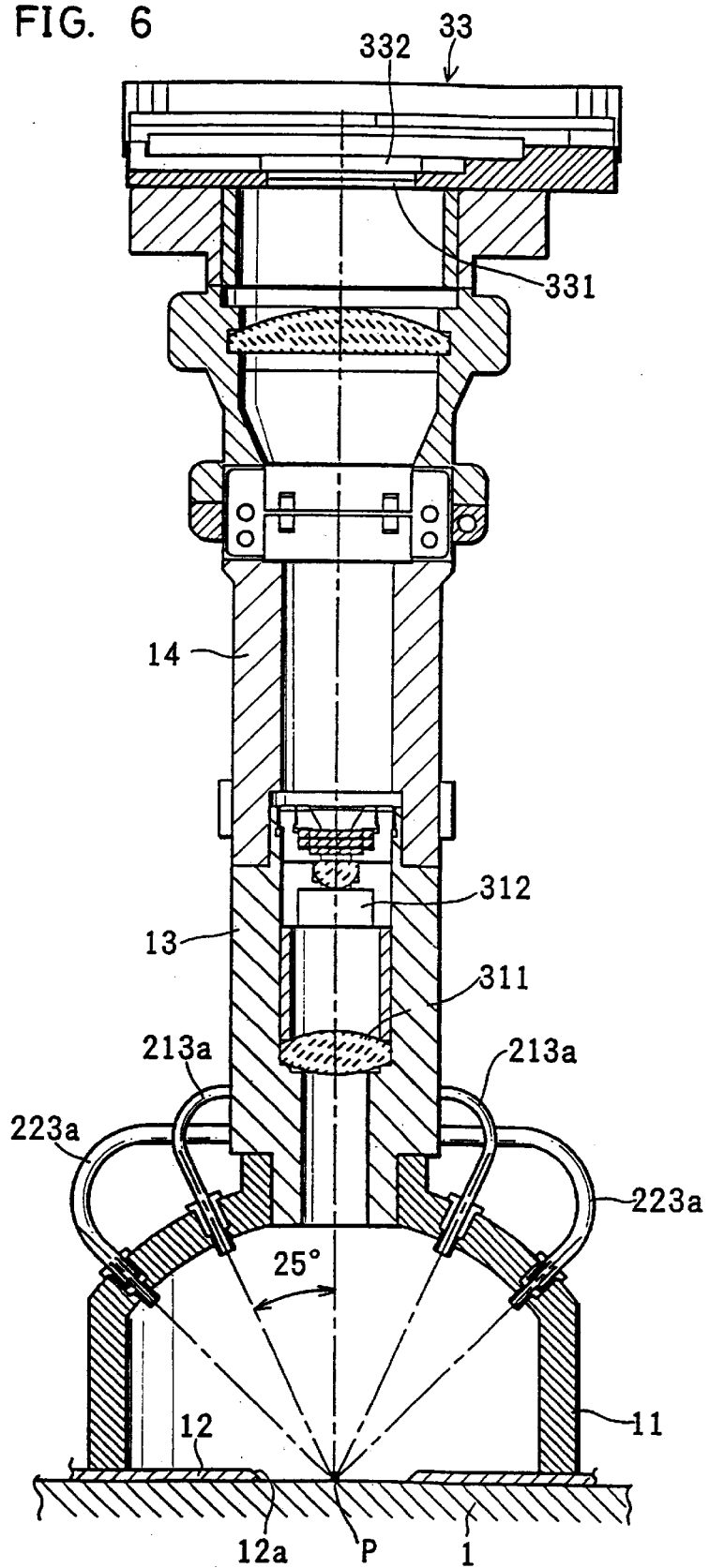
FIG. 6 is a diagram showing a color measuring apparatus according to another embodiment of the invention.

At the other end of the fiber bundle 213, the fiber bundle 213 is branched into eighteen optical fibers 213a, which are mounted on the optical base 11 so as to face the measurement area P of the object 1 and to be equally spaced along a circumference of an inverted cone about the measurement area P as shown in FIG. 5. In this embodiment, an angle of incidence of the illumination light on the measurement area P is set at 25° as shown in FIGS. 4 and 6. Accordingly, the illumination light incident on the fiber bundle 213 directly from the xenon lamp 211 and reflected by the reflector 212 is split into eighteen beams, which are projected to the measurement area P at a specified illumination angle (25°) in directions different from one another.

The radial illumination unit 22 basically has the same construction as the radial illumination unit 21 except that the angle of incidence of the illumination light on the measurement area P is set at 45°. Accordingly, no description is given to the construction of the radial illumination unit 22 by identifying the respective elements thereof by adding 10 to each of the corresponding reference numerals of the radial illumination unit 21.

The unidirectional illumination unit 23 is provided with a barrel 231 mounted at the side surface of the optical base 11 so as to emit light. A xenon lamp 232 which functions as a light source and a reflector 233 are mounted at one end of the barrel 231, and a projection lens 234 is arranged at the other end thereof. An optic axis of the projection lens 234 is set at 65° to a normal line N of the measurement area P. Thus, the illumination light directly emitted from the xenon lamp 232 or reflected by the reflector 233 is projected to the measurement area P at the specified illumination angle (65°) in a single direction. A hole 235 is formed in the side surface of the barrel 231 with a view to monitoring such illumination light. One end of an optical fiber 236 for monitoring is mounted in this hole 235, so that the illumination light can be introduced to the light receiving elements via this optical fiber 236.

Although the xenon lamp is used as a light source in any of the illumination units 21 to 23 in this embodiment, for example, tungsten lamps may be used instead of the xenon lamps. Further, the mount positions of the respective optical fibers 213a, 223a and the unidirectional illumination unit 23 are not limited to those shown in FIG. 4. They may be actually arranged in desired positions within the color measuring apparatus, especially utilizing optical lenses and optical fibers in this case.

In this color measuring apparatus, illumination light emitted from the radial illumination unit 21 or 22 or the unidirectional illumination unit 23 which is constructed as described above is reflected by the measurement area P, and the reflected light is received by either one of two unidirectional light receiving units 31, 32. In this embodiment, one spectral light receiving device 33 and a plurality of lenses for introducing reflected light to the spectral light receiving device 33 are used as common elements of the unidirectional light receiving units 31, 32. By drivingly controlling a movable mirror 34 provided in the second barrel 14 by a switch motor 35, the reflected light from the measurement area P can be received by either one of the light receiving units 31, 32.

Specifically, the unidirectional light receiving unit 31 includes first and second barrels 13, 14 for light reception which extend along the normal line N of the measurement area P, a lens 311 for light reception which faces the measurement area P in the first barrel 13, an aperture plate 312 arranged behind the lens 311, a plurality of lenses arranged in the second barrel 14 and the spectral light receiving device 33. When the movable mirror 34 is positioned in parallel with the normal line N along the inner wall of the second barrel 14, the light reflected by the measurement area P is introduced to the spectral light receiving device 33 via the lens 311, the aperture plate 312 and the plurality of lenses in the second barrel 14 and the spectral light receiving device 33 outputs an electrical signal corresponding to the reflected light.

Another unidirectional light receiving unit 32 includes a third barrel 321 for light reception which is mounted on the side surface of the optical base 11, a lens 322 for light reception which is so provided in the barrel 321 that its optic axis is at 45° to the normal line N, an aperture plate 323 arranged behind the lens 322, an optical fiber 324 for introducing reflected light from the third barrel 321 to the second barrel 14, the second barrel 14, the plurality of lenses provided in the second barrel 14 and the spectral light receiving device 33. When the movable mirror 34 is positioned such that it intersects with the normal line N at 45° in the second barrel 14, the light reflected by the measurement area P is incident on the optical fiber 324 via the lens 322 and the aperture plate 323, and is introduced to the second barrel 14 by the optical fiber 324. The reflected light is further introduced to the spectral light receiving device 33 via the movable mirror 34 and the plurality of lenses in the second barrel 14, and the spectral light receiving device 33 outputs an electrical signal corresponding to the reflected light.

The spectral light receiving device 33 includes a spectral filter 331 for separating reflected light introduced thereto as described above into beams of respective wavelengths, and light receiving elements 332, such as photodiodes, for receiving the beams of the respective wavelengths which have passed the spectral light receiving device 331 and outputting corresponding electrical signals. In other words, the spectral light receiving device 33 separates reflected light rays and outputs the electrical signals corresponding to the intensities of the reflected beams of the respective wavelengths.

With the spectral light receiving device 33 is connected with a control unit 4 for controlling the entire color measuring apparatus. More specifically, the output signal of the spectral light receiving device 33 is inputted to a CPU 42 after being converted into a digital signal in an analog-to-digital (A/D) converter 41. The CPU 42 performs a variety of calculations in accordance with a program stored in a ROM 43 in advance, thereby obtaining the color value of the measurement object 1 as described later. With the CPU 42 are electrically connected a RAM 44 for temporarily storing inputted information, the calculation results, etc. and a display device 45 for displaying color value and the like obtained by the calculations. The CPU 42 is also connected with an operation unit 47 and a buzzer 48 via an input/output (I/O) unit 46. The CPU 42 is further connected with first to third light emission circuits 49a to 49c for controllably turning the switch motor 35 and the xenon lamps 211, 221, 232 on and off. While the position of the movable mirror 34 is changed by controlling the switch motor 35, the first and third light emission circuits 49a to 49c are controlled to turn any of the three illumination units 21 to 23 on, with the result that the color value at a desired angle can be obtained. This will be described in detail later.

Figure 7:
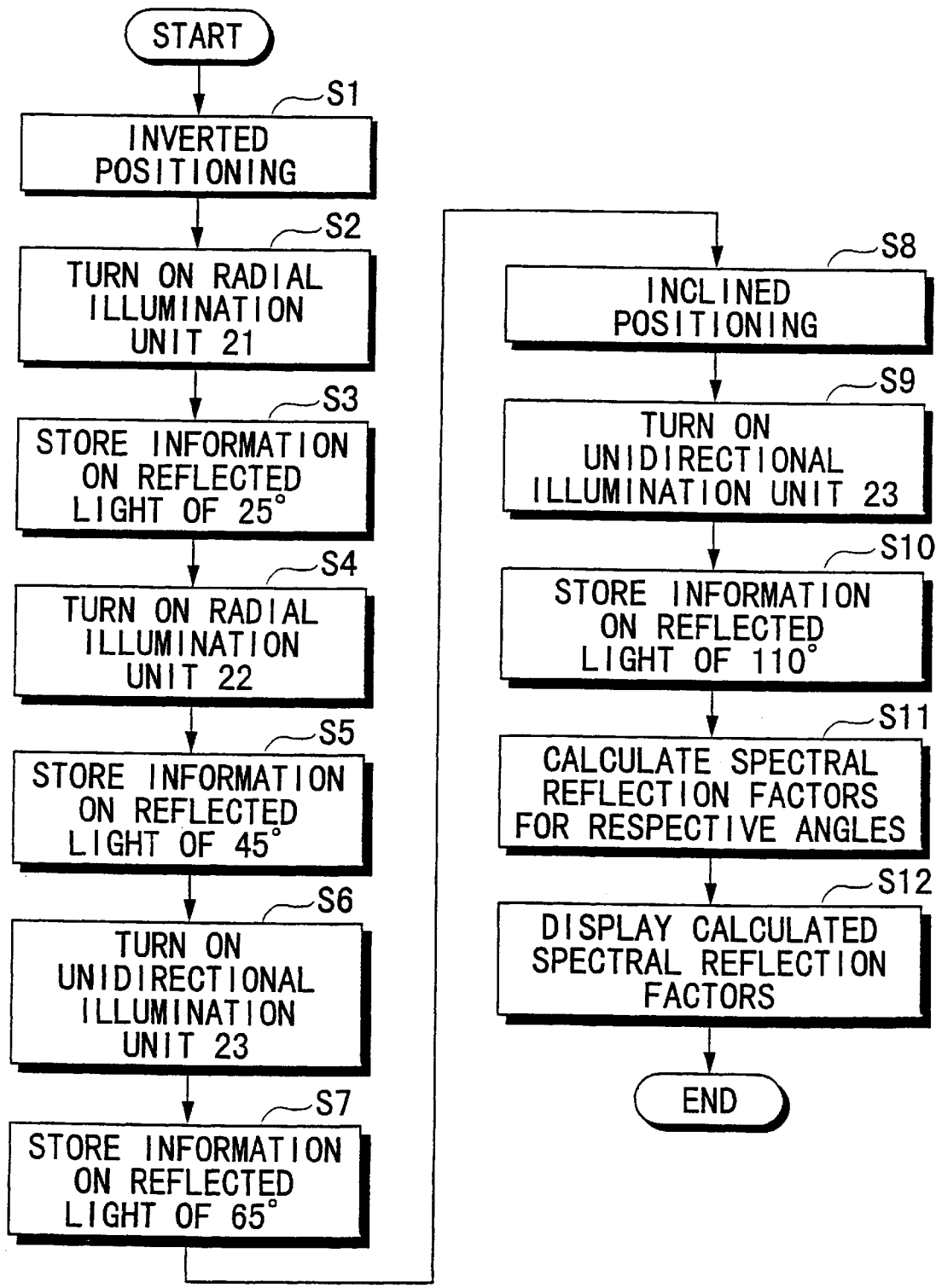
FIG. 7 is a flowchart showing an operation of the color measuring apparatus of FIG. 4.

Next, an operation of the color measuring apparatus constructed above will be described. FIG. 7 is a flowchart showing an operation of the color measuring apparatus of FIG. 4. As shown in FIG. 7, the movable mirror 34 is positioned in parallel with the normal line N along the inner wall of the second barrel 14 or inverted positioning is performed in Step S1. This enables the light reflected by the measurement area P to be received by the unidirectional light receiving unit 31, and the color values can be measured at 25°, 45° and 65° from the direction of regular reflection of the illumination light by turning any of the three illumination units 21 to 23 on and off.

Figure 8:
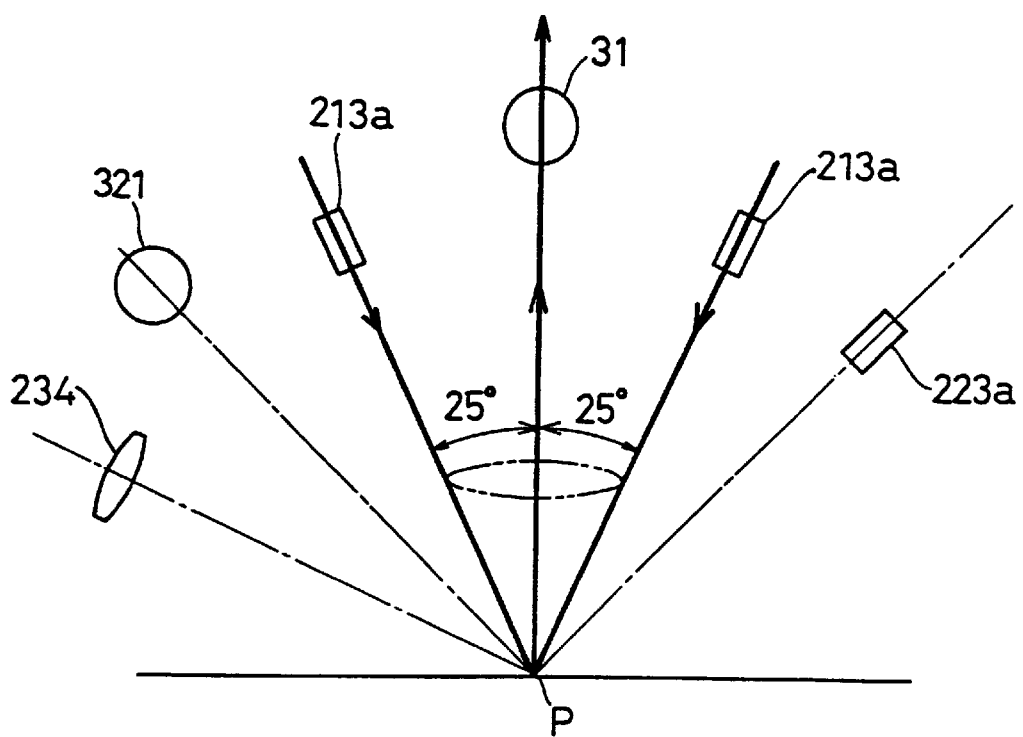
FIG. 8 is a diagram showing a relationship between illumination light rays emitted from radial illumination units (angle of incidence=25°) and reflected light rays introduced to unidirectional light receiving units.

Accordingly, in this embodiment, the xenon lamp 211 of the radial illumination unit 21 is selectively turned on (Step S2), so that, as shown in FIG. 8, illumination light rays are radially projected to the measurement area P at the angle of incidence (25°) in a plurality of directions different from each other and, out of illumination light rays reflected by the measurement area P, only the reflected light ray at 25° from the direction of regular reflection is selectively introduced to the unidirectional light receiving unit 31. This reflected light ray is received by the spectral light receiving device 33 and outputted to the controller 4 as an electrical signal representing the light intensity for each wavelength. This output signal is temporarily stored in the RAM 44 after being converted into a digital signal in the A/D converter 41. In this way, information on the reflected light ray at 25° from the direction of regular reflection is temporarily stored in the RAM 44 (Step S3).

Figure 9:
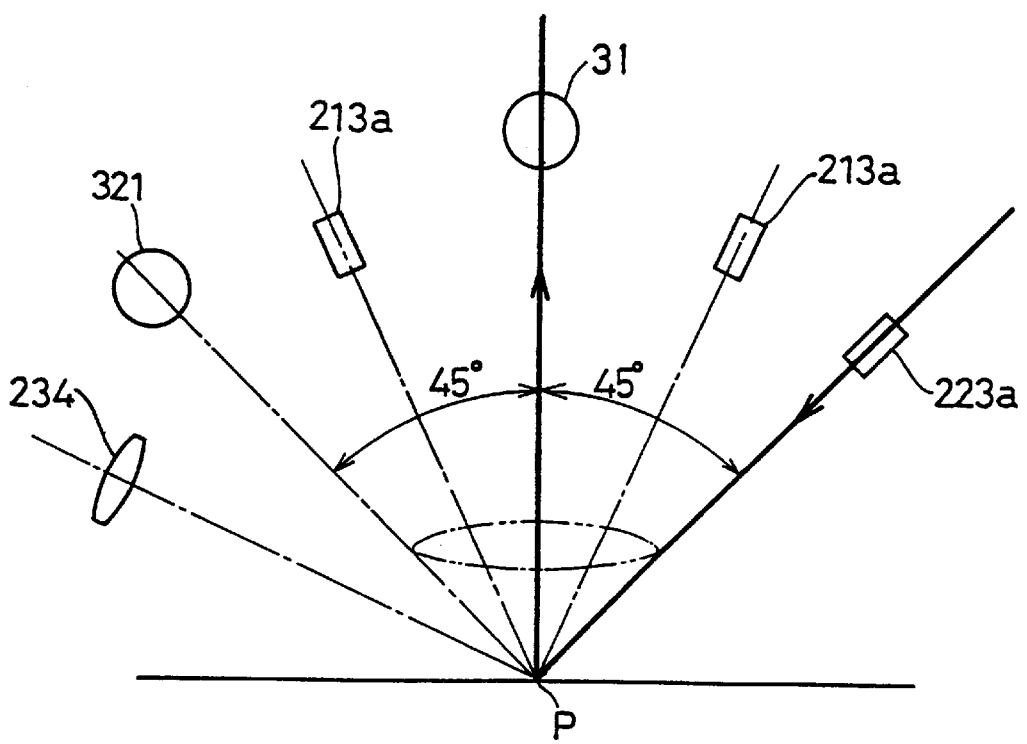
FIG. 9 is a diagram showing a relationship between illumination light rays emitted from the radial illumination units (angle of incidence=45°) and reflected light rays introduced to the unidirectional light receiving units.

Subsequently, the xenon lamp 221 of the radial illumination unit 22 is selectively turned on (Step S4), so that, as shown in FIG. 9, illumination light rays are radially projected to the measurement area P at the angle of incidence (45°) in a plurality of directions different from each other and, out of illumination light rays reflected by the measurement area P, only a reflected light ray at 45° from the direction of regular reflection is selectively introduced to the unidirectional light receiving unit 31. This reflected light ray is received by the spectral light receiving device 33 and outputted to the controller 4 as an electrical signal representing the light intensity for each wavelength. This output signal is temporarily stored in the RAM 44 after being converted into a digital signal in the A/D converter 41. In this way, information on a reflected light ray at 45° from the direction of regular reflection is temporarily stored in the RAM 44 (Step S5).

Figure 10:
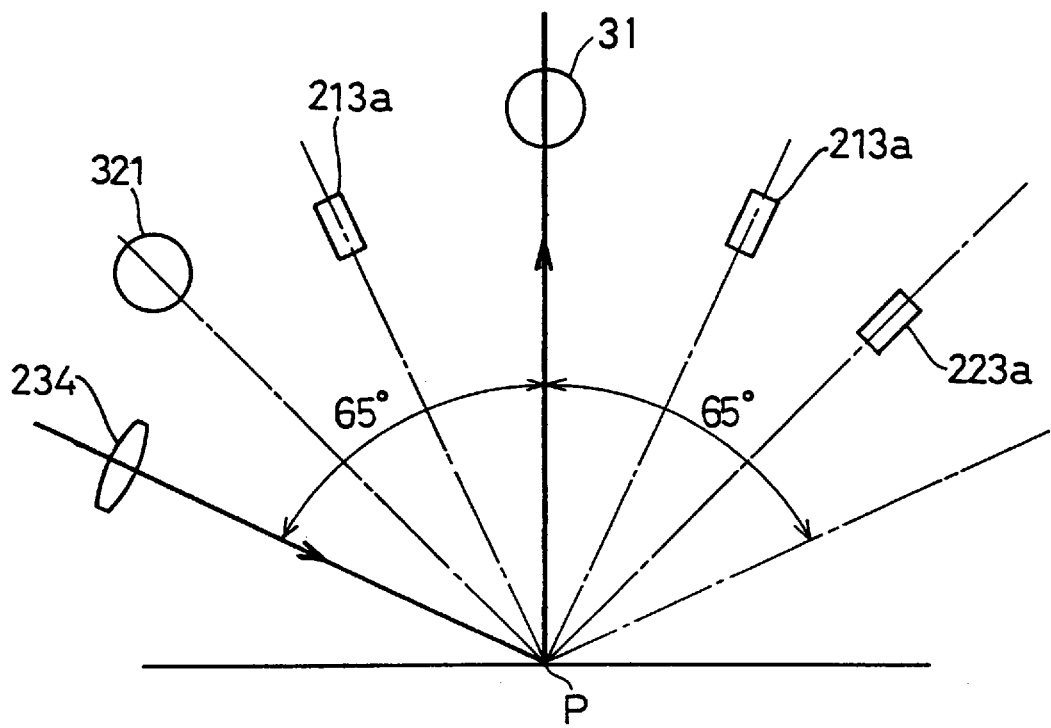
FIG. 10 is a diagram showing a relationship between illumination light rays emitted from unidirectional illumination units (angle of incidence=65°) and reflected light rays introduced to the unidirectional light receiving units.

Subsequently, the xenon lamp 232 of the unidirectional illumination unit 23 is selectively turned on (Step S6), so that, as shown in FIG. 10, illumination light rays are radially projected to the measurement area P at the angle of incidence (65°) in a specific direction (i.e., unidirectional illumination) and, out of illumination light rays reflected by the measurement area P, only a reflected light ray at 65° from the direction of regular reflection is selectively introduced to the unidirectional light receiving unit 31. This reflected light ray is received by the spectral light receiving device 33 and outputted to the controller 4 as an electrical signal representing the light intensity for each wavelength. This output signal is temporarily stored in the RAM 44 after being converted into a digital signal in the A/D converter 41. In this way, information on a reflected light ray at 65° from the direction of regular reflection is temporarily stored in the RAM 44 (Step S7).

Subsequently, in Step S8, the movable mirror 34 is so positioned as to intersect with the normal line N at 45° in the second barrel 14 by actuating the switch motor 35 (inclined positioning). This prevents the reflected light introduced along the normal line N in the first barrel 13 from propagating toward the spectral light receiving device 33. On the other hand, the reflected light introduced to the second barrel 14 via the lens 322, the aperture plate 323 and the optical fiber 324 is reflected by the movable mirror 34 to propagate toward the spectral light receiving device 33. In other words, by drivingly controlling the movable mirror 34, switching is made so that the reflected light can be received by the unidirectional light receiving unit 32.

Figure 11:
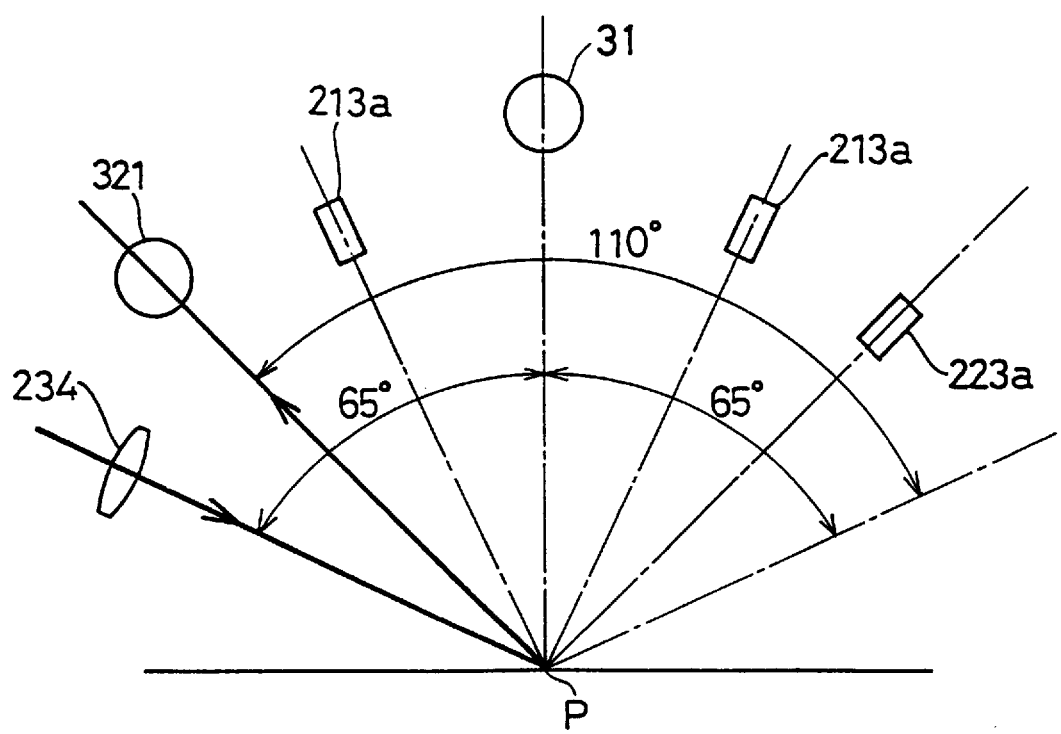
FIG. 11 is a diagram showing a relationship between illumination light rays emitted from unidirectional illumination units (angle of incidence=110°) and reflected light rays introduced to the unidirectional light receiving units.

Thereafter, the xenon lamp 232 of the unidirectional illumination unit 23 is selectively turned on (Step S9), so that, as shown in FIG. 11, the illumination light rays are radially projected to the measurement area P at the angle of incidence (110°) in a specific direction (i.e., unidirectional illumination) and, out of illumination light rays reflected by the measurement area P, only a reflected light ray at 110° from the direction of regular reflection is selectively introduced to the unidirectional light receiving unit 31. This reflected light ray is received by the spectral light receiving device 33 and outputted to the controller 4 as an electrical signal representing the light intensity for each wavelength. This output signal is temporarily stored in the RAM 44 after being converted into a digital signal in the A/D converter 41. In this way, information on the reflected light ray at 110° from the direction of regular reflection is temporarily stored in the RAM 44 (Step S10). Although the xenon lamp 232 is turned off after the execution of Step S6 in this embodiment, the xenon lamp 232 may be kept continuously on and the operation of Step S10 may be executed at the same time the movable mirror 34 is switched (Step S8).

After the pieces of information on the reflected light rays at 25°, 45°, 65° and 110° from the direction of regular reflection are measured in the above manner, these pieces of information are read from the RAM 44 and spectral reflection factors are successively calculated for the respective angles (Step S11). The calculated spectral reflection factors are displayed in the display device 45 as the color values of the measurement object 1 (Step S12).

As described above, in this embodiment, the measurements are performed based on the physical fact described in the "A-3. Study Based on the Measurement Results", i.e., color of a measurement object can be measured with substantially the same high accuracy regardless of whether the color measurement is performed by the radial illumination or the unidirectional illumination, in the case that color measurement is performed using reflected light rays relatively distant from the direction of regular reflection. Accordingly, for reflected light rays relatively distant from the direction of regular reflection, i.e., for a reflected light ray at 65°, the unidirectional illumination unit 23 is selectively turned on and the reflected light ray is received by the unidirectional light receiving unit 31. Thus, as compared with conventional color measuring apparatuses in which measurements are made by the radial illumination/unidirectional light reception or by the unidirectional illumination/radial light reception, the elements of the color measuring apparatus can be considerably reduced without reducing the measurement accuracy. This results in a simpler construction and a reduced production cost of the color measuring apparatus.

Further in this embodiment, the color-in-thickness measurement is also made possible by the measurement of unidirectional illumination/unidirectional light reception, thereby displaying a higher degree of versatility. This embodiment is not a mere combination of a color measuring apparatus capable of performing the color-in-thickness measurement of radial illumination/unidirectional light reception and a color measuring apparatus capable of performing the color-in-thickness measurement of unidirectional illumination/unidirectional light reception, but the color measuring apparatus is permitted to have a simpler construction and a lower production cost by commonly using a part of the elements.

Specifically, the color measuring apparatus according to this embodiment is constructed such that, whereas information on a reflected light ray at 65° from the direction of regular reflection is obtained by receiving reflected light rays by the unidirectional light receiving unit 31 while the measurement object 1 is illuminated by the unidirectional illumination unit 23, information on a reflected light ray at 110° from the direction of regular reflection is obtained by receiving reflected light rays by the unidirectional light receiving unit 32. Accordingly, the production cost of the color measuring apparatus having such a high degree of versatility can be reduced.

C. Other Embodiments (1) In the foregoing embodiment, the radial illumination is realized by the radial illumination units 21, 22 to perform a color measurement using reflected light rays (reflected light rays at 25°, 45°) relatively close to the direction of regular reflection, and a color measurement by the radial illumination/unidirectional light reception is made possible by receiving reflected light rays by the unidirectional light receiving unit 31. However, a color measurement may be performed by the unidirectional illumination/radial light reception by switching the illumination side and the light reception side.

(2) Although the other ends of the fiber bundles 213, 223 are branched into eighteen fibers to illuminate the measurement area P in eighteen directions different from each other in the foregoing embodiment, the number of the illumination directions is not limited to "eighteen", but may be any desired number over two.

(3) Although the angles of incidence of illumination light from the radial illumination units 21, 22 and the unidirectional illumination unit 23 are set at 25°, 45° and 65° respectively in the foregoing embodiment, the angles of incidence are not limited to them. For example, in the case that the unidirectional light receiving unit 31 is arranged on the normal line N as described above, the angle of incidence of illumination light rays from the radial illumination unit 21 may be set in a range of 10 to 35°, the angle of incidence of illumination light rays from the radial illumination unit 22 may be set in a range of 35 to 55°, and the angle of incidence of illumination light rays from the unidirectional illumination unit 23 may be set in a range of 55 to 80°. In such a case as well, a proper measurement can be performed similar to the foregoing embodiment.

(4) Further, the arrangement position of the third barrel 321 of the unidirectional light receiving unit 32 is not limited to the 45° position with respect to the normal line N (as in the foregoing embodiment). A proper measurement can be performed if the angle at which a reflected light ray is received by the unidirectional light receiving unit 32 lies within a range of 10 to 80°.

(5) In the foregoing embodiment, a reflected light ray is received by the spectral light receiving device 33 and the spectral reflection factor is calculated as the color value of the measurement object 1 based on the output signal of the spectral light receiving device 33. However, a light receiving device utilizing tristimulus value X, Y, Z may be used instead of the spectral light receiving device 33, and tristimulus values may be displayed in the display device 45 as the color value of a measurement object in accordance with a signal outputted from this light receiving device.

(6) Although pieces of information on reflected light rays at 4 different angles (25°, 45°, 65°, 110°) from the direction of regular reflection are obtained and the color value of the measurement object 1 is calculated for each angle in the foregoing embodiment, a combination of such angles is arbitrary.

As described in detail in the "A. Basic Principle of the Invention", the inventor of the present invention found out, for the first time, the physical fact that "the color of the measurement object can be measured with substantially the same high accuracy regardless of whether the color measurement of a measurement object is performed by the radial illumination or the unidirectional illumination or by the radial light reception or the unidirectional light reception, in the case that the color measurement is performed using a reflected light ray relatively distant from the direction of regular reflection. By applying this physical fact to the color measuring apparatus, the color measuring apparatus is permitted to have a simpler construction and a lower production cost.

According to the present invention, in order to perform a color measurement using a reflected light ray relatively distant from the direction of regular reflection, i.e., to obtain the color value at the second reflection angle $\theta 2$ (>$\theta 1$), illumination light from the unidirectional illumination unit is selectively projected to a measurement object and the color value at the second reflection angle $\theta 2$ is calculated based on the output from the unidirectional light receiving unit. This obviates the need to perform the radial illumination and the radial light reception as in the conventional color measuring apparatuses, thereby reducing the number of elements for the color measuring apparatus, thus simplifying the construction thereof and reducing the production cost thereof.

Further, the second unidirectional light receiving unit is additionally provided; illumination light from the unidirectional illumination unit is selectively projected to a measurement object; and the color value at the third reflection angle $\theta 3$ is calculated based on the output of the second unidirectional light receiving unit. Accordingly, a color-in-thickness measurement can also be performed by the same color measuring apparatus, thereby improving a degree of versatility. Furthermore, the unidirectional illumination unit is also used for the calculation of a color value at the second reflection angle $\theta 2$. Thus, the size and the production cost of the color measuring apparatus can be reduced by commonly using the elements.

Although the present invention has been fully described by way of example with reference to the accompanying drawings, it is to be understood that various changes and modifications will be apparent to those skilled in the art. Therefore, unless otherwise such changes and modifications depart from the scope of the present invention, they should be construed as being included therein.

What is claimed is:

1. An apparatus for measuring color of a measurement object, said apparatus comprising:
   a first radial illumination unit which projects illumination light to a measurement object at a first illumination angle in a plurality of directions different from one another;
   a unidirectional illumination unit which projects illumination light to the measurement object at a second illumination angle in a single direction, the second illumination angle being different from the first illumination angle;
   a first unidirectional light receiving unit which receives a light ray reflected at a first angle $\theta 1$ from the direction of regular reflection out of illumination light projected from the first radial illumination unit and reflected by the measurement object, and a light ray reflected at a second angle $\theta 2$ from the direction of regular reflection out of illumination light projected from the unidirectional illumination unit and reflected by the measurement object, the second angle $\theta 2$ being larger than the first angle $\theta 1$; and
   a processing unit which executes:
   1) calculation of a color value at the first angle $\theta 1$ based on an output of the first unidirectional light receiving unit by permitting the first radial illumination unit to project illumination light to the measurement object; and
   2) calculation of a color value at the second angle $\theta 2$ based on an output of the first unidirectional light receiving unit by permitting the unidirectional illumination unit to project illumination light to the measurement object.

2. An apparatus according to claim 1, further comprising a second unidirectional light receiving unit which receives a light ray reflected at a third angle $\theta 3$ from the direction of regular reflection out of illumination light projected from the unidirectional illumination unit and reflected by the measurement object, the third angle $\theta 3$ being equal to or larger than 90°, wherein the processing unit further executes calculation of a color value at the third angle $\theta 3$ based on an output of the second unidirectional light receiving unit by permitting the unidirectional illumination unit to project illumination light to the measurement object.

3. An apparatus according to claim 2, wherein the third angle $\theta 3$ is 110°.

4. An apparatus according to claim 2, wherein:
   the first unidirectional light receiving unit and the second unidirectional light receiving unit include a common spectral light receiver which receives a light ray reflected from the measurement object to output an electrical signal corresponding to the reflected light ray;
   the first unidirectional light receiving unit further includes a first light introducing member which introduces the reflected light ray to the common spectral light receiver;
   the second unidirectional light receiving unit further includes a second light introducing member which introduces the reflected light ray to the common spectral light receiver;
   the processing unit executes the calculation of a color value based on an electrical signal from the common spectral light receiver.

5. An apparatus according to claim 4, wherein the first unidirectional light receiving unit and the second unidirectional light receiving unit includes a changer which selectively changes over the introduction of reflected light ray through the first light introducing member and the introduction of reflected light ray through the second light introducing member.

6. An apparatus according to claim 2, wherein:
the first unidirectional light receiving unit and the second unidirectional light receiving unit include a common tristimulus value X, Y, Z light receiver which receives a light ray reflected from the measurement object to output an electrical signal corresponding to the reflected light ray;
the first unidirectional light receiving unit further includes a first light introducing member which introduces the reflected light ray to the common tristimulus value X, Y, Z light receiver;
the second unidirectional light receiving unit further includes a second light introducing member which introduces the reflected light ray to the common tristimulus value X, Y, Z light receiver;
the processing unit executes the calculation of a color value based on an electrical signal from the common tristimulus value X, Y, Z light receiver.

7. An apparatus according to claim 6, wherein the first unidirectional light receiving unit and the second unidirectional light receiving unit includes a changer which selectively changes over the introduction of reflected light ray through the first light introducing member and the introduction of reflected light ray through the second light introducing member.

8. An apparatus according to claim 2, further comprising a second radial illumination unit which projects illumination light to the measurement object at a third illumination angle in a plurality of directions different from one another, the third illumination angle being different from the first and second illumination angles, wherein the first unidirectional light receiving unit further receives a light ray reflected at a fourth angle $\theta 4$ from the direction of regular reflection out of illumination light projected from the second radial illumination unit and reflected by the measurement object, the fourth angle $\theta 4$ being larger than the first angle $\theta 1$ and being smaller than the second angle $\theta 2$, and the processing unit further executes calculation of a color value at the fourth angle $\theta 4$ based on an output of the first unidirectional light receiving unit by permitting the second radial illumination unit to project illumination light to the measurement object.

9. An apparatus according to claim 8, wherein the fourth angle $\theta 4$ is in a range between 35° and 55°.

10. An apparatus according to claim 9, wherein the fourth angle $\theta 4$ is 45°.

11. An apparatus according to claim 1, wherein the first angle $\theta 1$ is in a range between 10° and 35°, and the second angle $\theta 2$ is in a range between 55° and 80°.

12. An apparatus according to claim 11, wherein the first angle $\theta 1$ is 25°, and the second angle $\theta 2$ is 65°.

13. A method for measuring color of a measurement object, the method comprising the steps:
projecting illumination light to a measurement object at a first illumination angle in a plurality of directions different from one another;
receiving a light ray reflected at a first angle $\theta 1$ from the direction of regular reflection out of illumination light reflected by the measurement object;
outputting an electrical signal corresponding to the received light ray;
calculating a color value at the first angle $\theta 1$ based on the outputted electrical signal;

projecting illumination light to the measurement object at a second illumination angle in a single direction, the second illumination angle being different from the first illumination angle;
receiving a light ray reflected at a second angle $\theta 2$ from the direction of regular reflection out of illumination light reflected by the measurement object, the second angle $\theta 2$ being larger than the first angle $\theta 1$;
outputting an electrical signal corresponding to the received light ray; and
calculating a color value at the second angle $\theta 2$ based on the outputted electrical signal.

14. A method according to claim 13, further comprising the step of displaying a calculated color value at the first angle $\theta 1$ and a calculated color value at the second angle $\theta 2$.

15. A method according to claim 13, further comprising the steps of:
receiving a light ray reflected at a third angle $\theta 3$ from the direction of regular reflection out of illumination light projected at the second illumination angle in the single direction and reflected by the measurement object, the third angle $\theta 3$ being equal to or larger than 90°;
outputting an electrical signal corresponding to the received light ray; and
calculating a color value at the third angle $\theta 3$ based on the outputted electrical signal.

16. A method according to claim 15, further comprising the step of displaying a calculated color value at the first angle $\theta 1$, a calculated color value at the second angle $\theta 2$, and a calculated color value at the third angle $\theta 3$.

17. A method according to claim 15, further comprising the steps of:
projecting illumination light to the measurement object at a third illumination angle in a plurality of directions different from one another, the third illumination angle being different from the first and second illumination angles;
receiving a light ray reflected at a fourth angle $\theta 4$ from the direction of regular reflection out of illumination light reflected by the measurement object, the fourth angle $\theta 4$ being larger than the first angle $\theta 1$ and being smaller than the second angle $\theta 2$;
outputting an electrical signal corresponding to the received light ray; and
calculating a color value at the fourth angle $\theta 4$ based on the outputted electrical signal.

18. A method according to claim 17, further comprising the step of displaying a calculated color value at the first angle $\theta 1$, a calculated color value at the second angle $\theta 2$, a calculated color value at the third angle $\theta 3$, and a calculated color value at the fourth angle $\theta 4$.

19. A method according to claim 17, wherein the fourth angle $\theta 4$ is in a range between 35° and 55°.

20. A method according to claim 19, wherein the fourth angle $\theta 4$ is 45°.

21. A method according to claim 15, wherein the third angle $\theta 3$ is 110°.

22. A method according to claim 13, wherein the first angle $\theta 1$ is in a range between 10° and 35°, and the second angle $\theta 2$ is in a range between 55° and 80°.

23. A method according to claim 22, wherein the first angle $\theta 1$ is 25°, and the second angle $\theta 2$ is 65°.

* * * * *